United States Patent
Kobayashi

(10) Patent No.: US 10,226,408 B2
(45) Date of Patent: *Mar. 12, 2019

(54) HAIR DYE COMPOSITION AND METHOD FOR STABILIZING COLOR TONE OF HAIR DYE COMPOSITION

(71) Applicant: HOYU CO., LTD., Nagoya-shi, Aichi (JP)

(72) Inventor: Yosuke Kobayashi, Nagakute (JP)

(73) Assignee: Hoyu Co., Ltd., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/993,389

(22) Filed: Jan. 12, 2016

(65) Prior Publication Data

US 2016/0213583 A1   Jul. 28, 2016

(30) Foreign Application Priority Data

Jan. 22, 2015   (JP) .................................. 2015-010747

(51) Int. Cl.
  *A61Q 5/10* (2006.01)
  *A61K 8/34* (2006.01)
  *A61K 8/41* (2006.01)
  *A61K 8/19* (2006.01)

(52) U.S. Cl.
  CPC ................ *A61K 8/347* (2013.01); *A61K 8/19* (2013.01); *A61K 8/411* (2013.01); *A61K 8/415* (2013.01); *A61K 8/418* (2013.01); *A61Q 5/10* (2013.01); *A61K 2800/4324* (2013.01)

(58) Field of Classification Search
  CPC . A61Q 5/10; A61K 8/347; A61K 8/19; A61K 8/415; A61K 8/418; A61K 2800/4324
  See application file for complete search history.

(56) References Cited

U.S. PATENT DOCUMENTS

| | | | |
|---|---|---|---|
| 3,861,868 A | 1/1975 | Milbrada | |
| 6,432,147 B1 * | 8/2002 | Dias | A61K 8/22 8/406 |
| 7,182,791 B2 * | 2/2007 | Plos | A61K 8/46 568/327 |
| 2004/0083557 A1 * | 5/2004 | Au | A61Q 5/10 8/405 |
| 2005/0000035 A1 | 1/2005 | Chan et al. | |
| 2006/0117496 A1 | 6/2006 | Bolton et al. | |
| 2010/0269268 A1 | 10/2010 | Fukuhara et al. | |

FOREIGN PATENT DOCUMENTS

| | | |
|---|---|---|
| CA | 986019 A | 3/1976 |
| EP | 2201932 A1 | 6/2010 |
| JP | 2001-206825 | 7/2001 |
| JP | 2001-328926 | 11/2001 |
| JP | 2008-127343 | 6/2008 |
| WO | 2006/060567 A2 | 6/2006 |

OTHER PUBLICATIONS

Extended European Search Report dated May 10, 2016 in counterpart application EP-16152066.3.

* cited by examiner

*Primary Examiner* — Eisa B Elhilo
(74) *Attorney, Agent, or Firm* — Norris McLaughlin, P.A.

(57) ABSTRACT

A hair dye composition containing a carbonate also includes (A) at least one selected from resorcin and its derivatives, and salts thereof, an upper limit of a compounding amount of the component (A) being 0.2% by mass or less, and (B) at least one dye selected from 5-(2-hydroxyethylamino)-2-methylphenol, 1,5-dihydroxynaphthalene, and a nitro dye.

7 Claims, No Drawings

HAIR DYE COMPOSITION AND METHOD FOR STABILIZING COLOR TONE OF HAIR DYE COMPOSITION

BACKGROUND OF THE INVENTION

The present invention relates to a hair dye composition containing a carbonate and a method for stabilizing a color tone of hair dyed thereby.

Hair dye compositions capable of exhibiting effects upon mixing plural chemicals are known. As such hair dye compositions, there are known hair dye compositions constituted of a first agent containing, for example, an alkali agent and an oxidation dye and a second agent containing an oxidizing agent, for example, hydrogen peroxide. The dye can be properly chosen among known dyes from the viewpoints of desired color, lightness, chroma, and the like. For example, in the field of fashion color where high lightness and chroma are in general required, a hair dye composition in which a prescribed amount of 5-(2-hydroxyethylamino)-2-methylphenol, 1,5-dihydroxynaphthalene, or a nitro dye is compounded as a dye is used.

The alkali agent not only accelerates an action of the oxidizing agent to be contained in the second agent but also swells the hair to improve permeability of the dye into the hair, thereby improving hair dyeing power. There have hitherto been known ammonia and the like as the alkali agent to be used for the hair dye composition. However, there was involved such a problem that if a compounding amount of ammonia is increased, an irritant odor is accompanied therewith. There have hitherto been, for example, known hair dye compositions disclosed in JP-A-2001-206825, JP-A-2001-328926 and JP-A-2008-127343. According to JP-A-2001-206825, JP-A-2001-328926 and JP-A-2008-127343, by using ammonia and a carbonate in combination as the alkali agent, it is contemplated to not only make the compounding amount of ammonia lower than before but also improve hair dyeing power.

SUMMARY OF THE INVENTION

However, in the hair dye compositions in which a prescribed amount of 5-(2-hydroxyethylamino)-2-methylphenol, 1,5-dihydroxynaphthalene, or a nitro dye is compounded, there was a concern that stability of the dye is lowered. In particular, in the case of using a carbonate in combination, there was involved such a problem that there is a concern that stability of the dye is lowered due to such a carbonate.

Thus, an object of the present invention is to provide a hair dye composition containing a carbonate, which is capable of improving stability of the dye, and a method for stabilizing color tone of dyed hair.

The present invention is made on the basis of finding that in a hair dye composition containing a carbonate, by using resorcin or the like in combination, stability of the dye can be improved. It is to be noted that a numerical value expressing a content of each component in terms of % by mass is a numerical value in a dosage form including a solubilizer, such as water, and so forth.

In order to attain the above-described object, a first aspect of the present invention is concerned with a hair dye composition containing a carbonate, which comprises (A) at least one selected from resorcin and its derivatives, and salts thereof, an upper limit of a compounding amount of the component (A) being 0.2% by mass or less, and (B) at least one dye selected from 5-(2-hydroxyethylamino)-2-methylphenol, 1,5-dihydroxynaphthalene, and a nitro dye.

In the above-described hair dye composition, the component (A) may be contained in an amount of 0.005% by mass or more. The hair dye composition may further contain (C) a dye intermediate as an oxidation dye, thereby being constituted as a first agent for oxidation hair dye.

Another aspect of the present invention is concerned with a method for stabilizing a color tone of a hair dyed by a hair dye composition containing a carbonate in a first agent, the method comprising compounding, as the hair dye composition, (A) at least one selected from resorcin and its derivative, and salts thereof, an upper limit of a compounding amount of the component (A) being 0.2% by mass or less, and (B) at least one dye selected from 5-(2-hydroxyethylamino)-2-methylphenol, 1,5-dihydroxynaphthalene, and a nitro dye.

According to the present invention, it is possible to contemplate to improve the stability of the dye.

DETAILED DESCRIPTION OF THE INVENTION

An embodiment embodying the hair dye composition of the present invention is hereunder described.

A first agent for oxidation hair dye as a hair dye composition of the present embodiment (herein referred to simply as "first agent") is constituted as a first agent of a two-agent type oxidation hair dye composition. The two-agent type oxidation hair dye composition is, for example, constituted of a first agent containing at least a carbonate and an oxidation dye and a second agent containing at least an oxidizing agent. This oxidation hair dye composition is used for a hair dyeing treatment of hair after a mixture having the first agent and the second agent mixed therewith is prepared.

<First Agent>

In order to improve stability of the dye, the first agent contains (A) at least one selected from resorcin and its derivatives, and salts thereof, in addition to an alkali agent and a dye.

The carbonate is compounded from the viewpoint of improving the lightness. The carbonate is not particularly limited, and conventionally known carbonates, for example, sodium carbonate, sodium hydrogencarbonate, potassium carbonate, potassium hydrogencarbonate, lithium carbonate, calcium carbonate, magnesium carbonate, barium carbonate, guanidine carbonate, guanidine hydrogencarbonate, ammonium carbonate, and ammonium hydrogencarbonate can be used. Among those carbonates, only one may be contained solely, or a combination of two or more thereof may also be contained.

Though a lower limit of a content of the carbonate in the first agent is properly set, it is preferably 0.01% by mass or more, more preferably 0.1% by mass or more, and still more preferably 0.5% by mass or more. When the content of the carbonate is 0.01% by mass or more, in particular, the lightness can be more improved. In addition, in the case of using ammonia in combination as the alkali agent, by decreasing the compounding amount of ammonia, a reduction effect of an irritant odor originated from ammonia can also be expected.

Though an upper limit of the content of the carbonate in the first agent is properly set, it is preferably 20% by mass or less, more preferably 15% by mass or less, and still more preferably 10% by mass or less. When the content of the carbonate is 20% by mass or less, in particular, in the case of using a solubilizer, solubility against the solubilizer can be improved.

The alkali agent may be constituted of only the above-described carbonate, or an alkali agent other than the carbonate may also be used in combination. Examples of the alkali agent other than the carbonate include ammonia, an alkanolamine, a silicate, a metasilicate, a sulfate, a chloride, a phosphate, an organic amine, and a basic amino acid. Specific examples of the alkanolamine include monoethanolamine and triethanolamine. Specific examples of the silicate include sodium silicate and potassium silicate. Specific examples of the metasilicate include sodium metasilicate and potassium metasilicate. Specific examples of the sulfate include ammonium sulfate. Specific examples of the chloride include ammonium chloride. Specific examples of the phosphate include primary ammonium phosphate and secondary ammonium phosphate. Examples of the organic amine include 2-amino-2-methyl-1-propanol (AMP), 2-amino-2-methyl-1,3-propanediol, and guanidine. Specific examples of the basic amino acid include arginine and lysine. Among those alkali agents other than the carbonate, only one may be contained solely, or a combination of two or more thereof may also be contained. Of those, ammonia and an ammonium salt are preferably used from the viewpoint of improving a hair dyeing power.

In addition, in the case of using the alkali agent other than the carbonate in combination, though a mass ratio of the content of the carbonate to a content of the total alkali agent in the mixture of the first agent and the second agent is not particularly limited, it is preferably 0.2 or more, more preferably 0.3 or more, and still more preferably 0.4 or more from the viewpoint of exhibiting the reduction effect of an irritant odor in the case of using the carbonate. Namely, a proportion of the content of the alkali agent other than the carbonate in the total alkali agent is preferably 80% by mass or less, more preferably 70% by mass or less, and still more preferably 60% by mass or less. Though a lower limit of the proportion of the content of the alkali agent other than the carbonate in the total alkali agent is not particularly limited, it is preferably 0.1% by mass or more, and more preferably 0.3% by mass or more from the viewpoint of improving the lightness.

It is preferred that the alkali agent is compounded in an amount such that a pH of the mixture of the first agent and the second agent, namely the oxidation hair dye composition at the time of use is in the range of from 7 to 12. By regulating the pH of the mixture to 7 or more, the action of the oxidizing agent contained in the second agent can be more accelerated. By regulating the pH of the mixture to 12 or less, damaging of the hair can be more suppressed.

The first agent of the present embodiment contains, as the dye, (B) at least one dye selected from 5-(2-hydroxyethylamino)-2-methylphenol, 1,5-dihydroxynaphthalene, and a nitro dye. Among those specific examples of the dye, only one may be contained solely, or a combination of two or more thereof may also be contained. The 5-(2-hydroxyethylamino)-2-methylphenol and 1,5-dihydroxynaphthalene are a coupler of the oxidation dye. In addition, the nitro dye is one kind of direct dyes. When the component (B) is contained as the dye, the lightness and chroma are improved.

Examples of the nitro dye include 4-nitro-o-phenylenediamine, 2-nitro-p-phenylenediamine, 2-amino-4-nitrophenol, 2-amino-5-nitrophenol, picramic acid, picric acid, and salts thereof, as well as HC Blue No. 2, HC Blue No. 4, HC Blue No. 5, HC Blue NO. 6, HC Blue No. 8, HC Blue No. 9, HC Blue No. 10, HC Blue No. 11, HC Blue No. 12, HC Blue No. 13, HC Blue No. 14, HC Brown No. 1, HC Brown No. 2, HC Green No. 1, HC Orange No. 1, HC Orange No. 2, HC Orange No. 3, HC Orange No. 5, HC Red No. 1, HC Red No. 3, HC Red No. 7, HC Red No. 8, HC Red No. 9, HC Red No. 10, HC Red No. 11, HC Red No. 13, HC Red No. 14, HC Violet No. 1, HC Violet No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, and the like. Among those specific examples of the nitro dye, only one may be contained solely, or a combination of two or more thereof may also be contained. Among those specific examples of the nitro dye, 4-nitro-o-phenylenediamine, 2-nitro-p-phenylenediamine, HC Blue No. 2, and HC Yellow No. 4 are preferably applied from the viewpoint of improving the stability of color tone of dyed hair.

From the viewpoint that it is able to contemplate to make variations of the color tone easy or other viewpoint, it is preferred to incorporate two or more of the components (B). Though a lower limit of a content of the component (B) in the first agent is properly set, it is preferably 0.005% by mass or more, more preferably 0.01% by mass or more, and still more preferably 0.05% by mass or more. When the content of the component (B) is 0.005% by mass or more, in particular, the chroma can be more improved.

Though an upper limit of the content of the component (B) in the first agent is properly set, it is preferably 5% by mass or less, more preferably 3% by mass or less, and still more preferably 1% by mass or less. When the content of the component (B) is 5% by mass or less, in particular, the lightness can be more improved.

The first agent of the present embodiment contains an oxidation dye. The oxidation dye is a compound capable of undergoing color development induced by oxidative polymerization by the oxidizing agent contained in the second agent and is classified into a dye intermediate and a coupler which is bound with the dye intermediate to undergo color development. The first agent of the present embodiment contains (C) a dye intermediate as the oxidation dye. It is to be noted that it should be construed that the component (A) is not included in the coupler as the oxidation dye.

Examples of the dye intermediate (C) which is used in the present embodiment include p-phenylenediamine, toluene-2,5-diamine, p-aminophenol, N-phenyl-p-phenylenediamine, 4,4'-diaminodiphenylamine, o-aminophenol, p-methylaminophenol, N,N-bis(2-hydroxyethyl)-p-phenylenediamine, 2-hydroxyethyl-p-phenylenediamine, o-chloro-p-phenylenediamine, 4-amino-m-cresol, 2-amino-4-hydroxyethylaminoanisole, 2,4-diaminophenol, and derivatives thereof, and salts thereof. Among those specific examples of the dye intermediate, only one may be contained solely, or a combination of two or more thereof may also be contained. By using the dye intermediate (C), higher lightness and chroma can be obtained. In particular, in the field of fashion color where high lightness and chroma are required, a preferred color tone can be revealed.

Among those dye intermediates (C), at least one selected from p-phenylenediamine, toluene-2,5-diamine, p-aminophenol, and N,N-bis(2-hydroxyethyl)-p-phenylenediamine is preferred from the viewpoint that the lightness and chroma are excellent. Though a mass ratio of a content of at least one selected from p-phenylenediamine, toluene-2,5-diamine, and p-aminophenol to a content of the total dye intermediate in the first agent is not particularly limited, it is preferably 0.5 or more, more preferably 0.6 or more, and still more preferably 0.7 or more from the viewpoint of obtaining a color tone originated from such a preferred dye intermediate.

Though a lower limit of a content of the dye intermediate (C) in the first agent is properly set, it is preferably 0.001% by mass or more, more preferably 0.01% by mass or more, and still more preferably 0.02% by mass or more. When the content of the dye intermediate (C) is 0.001% by mass or more, in particular, the chroma can be more improved.

Though an upper limit of the content of the dye intermediate (C) in the first agent is properly set, it is preferably 5% by mass or less, more preferably 1% by mass or less, and still more preferably 0.5% by mass or less. When the content of the dye intermediate (C) is 5% by mass or less, the lightness and chroma can be more improved.

A coupler component other than the coupler contained in the component (B) may be used in combination within the range where the effects of the present invention are not impaired. Examples of such a coupler include 5-amino-o-cresol, m-aminophenol, α-naphthol, m-phenylenediamine, 2,4-diaminophenoxyethanol, toluene-3,4-diamine, 2,6-diaminopyridine, diphenylamine, N,N-diethyl-m-aminophenol, phenylmethylpyrazolone, and salts thereof. Furthermore, as the 2,4-diaminophenoxyethanol, for example, there is exemplified 2,4-diaminophenoxyethanol hydrochloride. Among those specific examples of the coupler, only one may be contained solely, or a combination of two or more thereof may also be contained.

In addition, though a mass ratio of the content of the coupler contained in the component (B) to a content of the total coupler in the first agent is not particularly limited, it is preferably 0.2 or more, and more preferably 0.3 or more from the viewpoint of obtaining a color tone originated from the coupler contained in the component (B).

The first agent may further properly contain an oxidation dye published in, for example, *Japanese Standards of Quasi-drug Ingredients* (published by Yakuji Nippo Limited in June 2006) as a dye other than the above-described oxidation dye.

Though a lower limit of the content of the total dye in the first agent is properly set, it is preferably 0.01% by mass or more, more preferably 0.05% by mass or more, and still more preferably 0.08% by mass or more. When the content of the total oxidation dye is 0.01% by mass or more, in particular, the chroma can be more improved.

Though an upper limit of the content of the total oxidation dye in the first agent is properly set, it is preferably 10% by mass or less, more preferably 7% by mass or less, and still more preferably 5% by mass or less. When the content of the total dye is 10% by mass or less, in particular, in the case of using a solubilizer, solubility against the solubilizer can be improved. In addition, in particular, the lightness can be more improved.

In the first agent, (A) at least one selected from resorcin and its derivatives, and salts thereof is compounded. Examples of the derivative of resorcin include an alkylated resorcin, a halogenated resorcin, and the like. Specific examples of the alkylated resorcin include 2-methylresorcin and the like. Specific examples of the halogenated resorcin include 4-chlororesorcin, 2-chlororesorcin, and the like. Among those resorcins, only one may be contained solely, or a combination of two or more thereof may also be contained. In the constitution containing a carbonate in the first agent, the component (A) improves the stability of the above-described dye, particularly the component (B).

Though a lower limit of a content of the component (A) in the first agent is properly set, it is preferably 0.005% by mass or more, more preferably 0.01% by mass or more, and still more preferably 0.03% by mass or more. When the content of the component (A) is 0.005% by mass or more, the stability of the above-described component (B) can be more improved.

An upper limit of the content of the component (A) in the first agent is 0.2% by mass or less, preferably 0.15% by mass or less, and more preferably 0.1% by mass or less. When the content of the component (A) is 0.2% by mass or less, revelation of a color tone originated from the component (A) can be suppressed, and the chroma can be more improved.

Though a mass ratio of the content of the component (B) to the content of the component (A) in the first agent is not particularly limited, a lower limit thereof is preferably 0.1 or more, more preferably 0.2 or more, and still more preferably 0.4 or more. When such a mass ratio is 0.1 or more, in particular, the chroma can be more improved. Though an upper limit of the mass ratio of the content of the component (B) to the content of the component (A) in the first agent is properly set, it is preferably 12 or less, more preferably 11 or less, and still more preferably 10 or less. When such a mass ratio is 12 or less, in particular, the lightness can be more improved.

In addition to the above-described components, for example, a solubilizer, a water-soluble polymer compound, an oil component, a polyhydric alcohol, a surfactant, a sugar, an antiseptic, a stabilizer, a pH adjustor other than those described above, a plant extract, a crude drug extract, a vitamins, a perfume, an antioxidant, an ultraviolet ray absorber, a chelating agent, and an oxidation aid can be further contained in the first agent, if desired.

The solubilizer is, for example, compounded in the case of rendering the first agent in a liquid form. Examples of the solubilizer to be used include water and an organic solvent (solvent). Specific examples of the organic solvent include ethanol, n-propanol, isopropanol, methyl cellosolve, ethyl cellosolve, methyl carbitol, ethyl carbitol, benzyl alcohol, phenethyl alcohol, γ-phenylpropyl alcohol, cinnamic alcohol, anise alcohol, p-methylbenzyl alcohol, α-dimethylphenethyl alcohol, α-phenylethanol, phenoxyethanol, phenoxyisopropanol, 2-benzyloxyethanol, an N-alkylpyrrolidone, an alkylene carbonate, and an alkyl ether. Among those solubilizers, only one may be contained solely, or a combination of two or more thereof may also be contained. Among them, water is preferably used because it is excellent in ability of dissolving other components in the first agent. In the case of using water as the solvent, a content of water (content at the time of use) in the mixture of the first agent and the second agent is preferably 50% by mass or more, and more preferably 60% by mass or more.

The water-soluble polymer compound gives an appropriate viscosity to the mixture. Specific examples of the water-soluble polymer compound include a natural polymer, a semi-synthetic polymer, a synthetic polymer, and an inorganic material-based polymer. Examples of the natural water-soluble polymer compound include guar gum, locust bean gum, quince seed, carrageenan, galactan, gum arabic, tragacanth gum, pectin, mannan, xanthan gum, dextran, succinoglucan, curdlan, hyaluronic acid, gelatin, casein, albumin, and collagen.

Examples of the semi-synthetic water-soluble polymer compound include methyl cellulose, ethyl cellulose, hydroxyethyl cellulose, hydroxyethyl cellulose dimethyldiallyl ammonium chloride, hydroxypropyl cellulose, carboxymethyl cellulose, sodium carboxymethyl cellulose, hydroxypropyl methylcellulose, cationized cellulose, cationized guar gum, starch phosphate ester, alginic acid propylene glycol ester, and an alginate.

Examples of the synthetic water-soluble polymer compound include polyvinyl alcohol, polyvinyl pyrrolidone, polyvinyl methyl ether, a carboxyvinyl polymer, sodium polyacrylate, polyacrylamide, polyethylene oxide, an ethylene oxide-propylene oxide block copolymer, an acrylic acid-alkyl acrylate copolymer, and polychlorinated dimethylmethylene piperidinium. In addition, as the synthetic polymer, there is exemplified a copolymer composed of a half ester of itaconic acid and a polyoxyethylene alkyl ether or an ester of methacrylic acid and a polyoxyethylene alkyl ether, and at least one monomer selected from acrylic acid, methacrylic acid, and alkyl esters thereof. Among those water-soluble polymer compounds, only one may be contained solely, or a combination of two or more thereof may also be contained.

The oil component gives a moist touch to a hair. For that reason, the first agent contains an oil component within the range where the effects of the present invention are not impaired. Examples of the oil component include a fat and oil, a wax, a higher alcohol, a hydrocarbon, a higher fatty acid, an alkyl glyceryl ether, an ester, and a silicone.

Examples of the fat and oil include lanolin, olive oil, camellia oil, shea butter, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil. Examples of the wax include bee wax, candelilla wax, carnauba wax, jojoba oil, and lanolin. Examples of the higher alcohol include cetyl alcohol (cetanol), 2-hexyldecanol, stearyl alcohol, isostearyl alcohol, cetostearyl alcohol, oleyl alcohol, arachyl alcohol, behenyl alcohol, 2-octyldodecanol, lauryl alcohol, myristyl alcohol, decyltetradecanol, and lanolin alcohol.

Examples of the hydrocarbon include paraffin, an olefin oligomer, polyisobutene, hydrogenated polyisobutene, a mineral oil, squalane, polybutene, polyethylene, microcrystalline wax, and vaseline. Examples of the higher fatty acid include lauric acid, myristic acid, palmitic acid, stearic acid, behenic acid, isostearic acid, 12-hydroxystearic acid, oleic acid, and lanolin fatty acid. Examples of the alkyl glyceryl ether include batyl alcohol, chimyl alcohol, selachyl alcohol, and isostearyl glyceryl ether.

Examples of the ester include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, a fatty acid cholesteryl/lanosteryl having 10 to 30 carbon atoms, cetyl lactate, lanolin acetate, ethylene glycol di-2-ethylhexanoate, a pentaerythritol fatty acid ester, a dipentaerythritol fatty acid ester, cetyl caprate, glyceryl tricaprylate, diisostearyl malate, dioctyl succinate, and cetyl 2-ethylhexanoate.

Examples of the silicone include dimethylpolysiloxane (dimethicone), methylphenylpolysiloxane, decamethylcyclopentasiloxane, dodecamethylcyclohexasiloxane, hydroxyl group-terminated modified dimethylpolysiloxane, a highly polymerized silicone, polyether-modified silicone (for example, a (PEG/PPG/butylene/dimethicone) copolymer), an amino-modified silicone, a betaine-modified silicone, alkyl-modified silicone, alkoxy-modified silicone, a mercapto-modified silicone, a carboxy-modified silicone, and a fluorine-modified silicone. Among those oil components, only one may be contained solely, or a combination of two or more thereof may also be contained.

Examples of the polyhydric alcohol include a glycol and a glycerin. Examples of the glycol include ethylene glycol, diethylene glycol, triethylene glycol, polyethylene glycol, propylene glycol, dipropylene glycol, isoprene glycol, and 1,3-butylene glycol. Examples of the glycerin include glycerin, diglycerin, and polyglycerin. Among those polyhydric alcohols, only one may be contained solely, or a combination of two or more thereof may also be contained.

The surfactant plays a role as an emulsifier or a component of solubilizing each of the components to emulsify or solubilize the oxidation hair dye composition at the time of use, thereby adjusting the viscosity or improving the stability of viscosity. Examples of the surfactant include an anionic surfactant, a cationic surfactant, an amphoteric surfactant, and a nonionic surfactant.

Examples of the anionic surfactant include an alkyl ether sulfate, an alkyl sulfate, an alkyl ether sulfate ester salt, an alkenyl ether sulfate, an alkenyl sulfate, an olefin sulfonate, an alkane sulfonate, a saturated or unsaturated fatty acid salt, an alkyl or alkenyl ether carboxylate, an α-sulfone fatty acid salt, an N-acylamino acid type surfactant, a phosphoric acid mono- or diester type surfactant, a sulfosuccinic acid ester, and derivatives thereof. Examples of a counter ion for the anionic group in such a surfactant include a sodium ion, a potassium ion, and triethanolamine. More specifically, examples of the alkyl ether sulfate salt include polyoxyethylene (hereinafter referred to as "POE") lauryl ether sodium sulfate. Examples of the alkyl sulfate include sodium lauryl sulfate and sodium cetyl sulfate. Examples of the derivative of alkyl sulfate include sodium POE lauryl sulfate. Examples of the sulfosuccinic acid ester include disodium lauryl sulfosuccinate.

Examples of the cationic surfactant include lauryl trimethyl ammonium chloride, cetyl trimethyl ammonium chloride, stearyl trimethyl ammonium chloride, an alkyl trimethyl ammonium chloride, distearyl dimethyl ammonium chloride, cetyl trimethyl ammonium bromide, stearyl trimethyl ammonium bromide, a lanolin fatty acid aminopropylethyldimethyl ammonium ethyl sulfate, stearyl trimethyl ammonium saccharine, cetyl trimethyl ammonium saccharine, methacryloyloxyethyl trimethyl ammonium chloride, and behenyl trimethyl ammonium methyl sulfate.

Specific examples of the amphoteric surfactant include coco-betaine, lauramidopropyl betaine, cocamidopropyl betaine, sodium lauroamphoacetate, sodium cocoamphoacetate, coconut oil fatty acid amide propyl betaine, and lauryl betaine (lauryl dimethylaminoacetic acid betaine).

Specific examples of the nonionic surfactant include an ether type nonionic surfactants, an ester type nonionic surfactant, and an alkyl glucoside. Specific examples of the ether type nonionic surfactant include POE cetyl ether (Ceteth), POE stearyl ether (Steareth), POE behenyl ether, POE oleyl ether (Oleth), POE lauryl ether (Laureth), POE octyldodecyl ether, POE hexyldecyl ether, POE isostearyl ether, POE nonylphenyl ether, and POE octylphenyl ether.

Specific examples of the ester type nonionic surfactant include POE sorbitan monooleate, POE sorbitan monostearate, POE sorbitan monopalmitate, POE sorbitan monolaurate, POE sorbitan trioleate, POE glycerin monostearate, POE glycerin monomyristate, POE sorbitol tetraoleate, POE sorbitol hexastearate, POE sorbitol monolaurate, POE sorbitol bee wax, polyethylene glycol monooleate, polyethylene glycol monostearate, polyethylene glycol monolaurate, lipophilic glycerin monooleate, lipophilic glycerin monostearate, self-emulsifying glycerin monostearate, sorbitan monooleate, sorbitan sesquioleate, sorbitan trioleate, sorbitan monostearate, sorbitan monopalmitate, sorbitan monolaurate, a sucrose fatty acid ester, decaglyceryl monolaurate, decaglyceryl monostearate, decaglyceryl monooleate, and decaglyceryl monomyristate.

Examples of the alkyl glucoside include an alkyl (having 8 to 16 carbon atoms) glucoside, POE methyl glucoside, and POE dioleate methyl glucoside. Among those surfactants, only one may be contained solely, or a combination of two or more thereof may also be contained.

Examples of the sugar include monosaccharides, such as glucose, galactose, etc., disaccharides, such as maltose, sucrose, fructose, trehalose, etc., and sugar alcohols. Examples of the antiseptic include paraben. Examples of the stabilizer include phenacetin, 8-hydroxyquinoline, acetanilide, sodium pyrophosphate, barbituric acid, uric acid, and tannic acid. Examples of the pH adjustor include citric acid, tartaric acid, lactic acid, malic acid, succinic acid, fumaric acid, maleic acid, pyrophosphoric acid, gluconic acid, glucuronic acid, benzoic acid, and the like. Examples of the antioxidant include ascorbic acid and a sulfite. Examples of the chelating agent include edetic acid (ethylenediaminetetraacetic acid (EDTA)), edetate disodium, edetate tetrasodium, diethylenetriaminepentaacetic acid and a salt thereof, ethylenediaminehydroxyethyltriacetic acid and a salt thereof, and hydroxyethanediphosphonic acid (HEDP) and a salt thereof.

A dosage form of the first agent is not particularly limited, and specific examples thereof include a liquid form, a gel form, a foamy form, a cream form, and a solid form. Examples of the liquid form include an aqueous solution, a dispersion liquid, and an emulsion.

<Second Agent>

In the second agent, the above-described solubilizer or the like can also be compounded in addition to an oxidizing agent. The oxidizing agent more improves decolorizing properties of melanin contained in a hair. Specific examples of the oxidizing agent include hydrogen peroxide, urea peroxide, melamine peroxide, sodium percarbonate, potassium percarbonate, sodium perborate, potassium perborate, ammonium persulfate, potassium persulfate, sodium persulfate, sodium peroxide, potassium peroxide, magnesium peroxide, barium peroxide, calcium peroxide, strontium peroxide, a hydrogen peroxide adduct of sulfate, a hydrogen peroxide adduct of phosphate, and a hydrogen peroxide adduct of pyrophosphate. Among those oxidizing agents, only one may be contained solely, or a combination of two or more thereof may also be contained. Though a content of the oxidizing agent in the second agent is properly set, it is preferably 0.1% by mass or more, more preferably 2.0% by mass or more, and still more preferably 3.0% by mass or more. In the case where the content of the oxidizing agent is 0.1% by mass or more, the decolorizing properties of melanin can be more improved. In addition, the content of the oxidizing agent in the second agent is preferably 15.0% by mass or less, more preferably 9.0% by mass or less, and still more preferably 6.0% by mass or less. In the case where the content of the oxidizing agent is 15.0% by mass or less, damaging or the like of the hair can be more suppressed.

In the case where hydrogen peroxide is compounded as the oxidizing agent in the second agent, for the purpose of improving the stability of hydrogen peroxide, the second agent preferably contains a stabilizer, for example, ethylene glycol phenyl ether (phenoxyethanol) and hydroxyethanediphosphonic acid or a salt thereof. Examples of the salt of hydroxyethanediphosphonic acid include tetrasodium hydroxyethanediphosphonate and disodium hydroxyethanediphosphonate. The second agent may contain each component which is generally contained in an oxidation hair dye composition and which does not impair the action of each of the components. For example, the components which are contained in the above-described first agent may be properly contained within the range where the effects of the present invention are not impaired.

A dosage form of the second agent is not particularly limited, and specific examples thereof include a liquid form, a gel form, a foamy form, a cream form, and a solid form. Examples of the liquid form include an aqueous solution, a dispersion liquid, and an emulsion. At the time of using the oxidation hair dye composition, a mixture is prepared by mixing the first agent and the second agent. Subsequently, the mixture in a necessary amount is applied to a hair by hands using thin-gloves or with a comb or brush.

Next, the action of the first agent of the present embodiment is described.

For example, there was a concern that in 5-(2-hydroxyethylamino)-2-methylphenol, 1,5-dihydroxynaphthalene, or a nitro dye, which is used in the field of fashion color where high lightness and chroma are in general required, the stability of the dye is lowered. In particular, when used in combination with a carbonate, there was a concern that the storage stability is lowered, so that the color tone after the hair dyeing treatment changes. For example, when the compounding amount of the dye is increased, there may be the case where the dye is stabilized. However, the lightness changes toward the direction of decrease. Thus, it was not easy to improve the stability of the dye while obtaining the desired lightness. According to the present invention, by further adding a specified amount of (A) an aromatic compound, such as resorcin, etc., even in the case of long-term storage, the storage stability of 5-(2-hydroxyethylamino)-2-methylphenol, 1,5-dihydroxynaphthalene, or a nitro dye can be improved, whereby the change of the color tone of a dyed hair can be suppressed. In addition, since it is not necessary to adjust the compounding amount of the dye for the purpose of improving the stability of the dye, the change of the color tone can be suppressed from such a viewpoint, too.

The first agent according to the present embodiment brings about the following advantages.

(1) In the present embodiment, in the constitution containing a carbonate in the first agent, a specified amount of (A) resorcin or the like was used in combination. Accordingly, the stability of a dye, more specifically (B) at least one dye selected from 5-(2-hydroxyethylamino)-2-methylphenol, 1,5-dihydroxynaphthalene, and a nitro dye, can be improved. Therefore, even in the case of long-term storage, the change of the color tone of a dyed hair can be suppressed.

(2) In the case where the first agent further contains the dye intermediate (C) as the oxidation dye, the lightness and chroma can be more improved. In particular, in the field of fashion color where high lightness and chroma are required, the first agent of the present embodiment can be suitably used.

The above-described embodiment may also be modified in the following manners.

The hair dye composition of the above-described embodiment was constituted as a first agent for oxidation hair dye. In the hair dye composition of the above-described embodiment, a constitution in which the dye intermediate (C) is not compounded as the dye may also be adopted. For example, the hair dye composition may be constituted as a semi-permanent hair dye containing a carbonate, the component (A), an upper limit of a compounding amount thereof being 0.2% by mass or less, and a nitro dye as the component (B) without using the dye intermediate (C) and the oxidizing agent.

In the above-described embodiment, a direct dye other than the nitro dye, as published in, for example, *Japanese Standards of Quasi-drug Ingredients* (published by Yakuji Nippo Limited in June 2006) may be properly contained as a dye other than the above-described dye within the range where the effects of the present invention are not impaired.

In the above-described embodiment, a multiagent type oxidation hair dye composition comprising the first agent containing a carbonate and a dye, etc. and a second agent containing an oxidizing agent, etc. was constituted. However, so long as the carbonate and the components (A) and (B) are compounded in the same agent, the oxidation hair dye composition is not limited to a two-agent type but may be constituted as a plural-agent type, for example, a three- or more-agent type by constituting a part of the respective components contained in the first agent and the second agent as a separate agent.

In the above-described embodiment, though the field to which the first agent is applied is not particularly limited, the first agent of the present embodiment can be preferably applied in the field of fashion color where high lightness and chroma are in general required.

EXAMPLES

Next, the above-described embodiments are more specifically described by reference to Examples and Comparative Examples. It is to be noted that the present invention is not limited to the constitutions described in the Examples.

Formulation Example 1

In Formulation Example 1, the hair dye composition of the present embodiment was constituted as a first agent in a cream form of an oxidation hair dye composition. A first agent and a second agent of an oxidation hair dye composition, each containing respective components shown in Tables 1 and 2, were prepared. Numerical values in the columns expressing the respective components in Tables 1 and 2 show contents of components in the instant columns, and units thereof are % by mass (the same in Tables 3 et seq.) Then, the first agent and the second agent were mixed in a mass ratio of 1/1 to prepare an oxidation hair dye composition. The obtained oxidation hair dye composition was applied to a bundle of human black hair (15 cm, available from Beaulax Co., Ltd.) (herein referred to simply as "hair bundle") by using a brush and then allowed to stand at room temperature (25° C.) for 30 minutes. Subsequently, the oxidation hair dye composition attached onto the hair bundle was washed off with water, and thereafter, the hair bundle was applied with a shampoo ("Bigen Treatment Shampoo", available from Hoyu Co., Ltd.) twice and a rinse ("Bigen Treatment Rinse", available from Hoyu Co., Ltd.) once. Subsequently, the hair bundle was dried with warm air and then allowed to stand for one day. The hair bundle to which the hair dyeing treatment had been applied was evaluated with respect to lightness and chroma according to the following methods. In addition, the first agent of each of the Examples and Comparative Examples was preserved for a prescribed period of time. The hair bundle having been thus subjected to the hair dyeing treatment was evaluated with respect to a change of color tone of dyed hair according to the following method. It is to be noted that the expressions (A) to (C) in the "Component" column in the tables express the compounds corresponding to the respective components as described in the claims of the present application.

<Lightness>

The lightness of the human hair bundle having been treated with each of the oxidation hair dye compositions was visually observed under a standard light source by ten expert panelists and marked with three grades of a score 3, a score 2, and a score 1. The higher the score is, the better the evaluation result is. With respect to the marking results by each of the expert panelists, an average value was calculated. The evaluation results are designated in such a manner that the case where the average value was 2.6 or more is defined as "A"; the case where the average value was 1.6 or more and less than 2.6 is defined as "B"; and the case where the average value was less than 1.6 is defined as "C". The results are shown in Table 1.

<Chroma>

The chroma of the human hair bundle having been treated with each of the oxidation hair dye compositions was visually observed under a standard light source by ten expert panelists and marked with three grades of a score 3, a score 2, and a score 1. The higher the score is, the better the evaluation result is. With respect to the marking results by each of the expert panelists, an average value was calculated. The evaluation results are designated in such a manner that the case where the average value was 2.6 or more is defined as "A"; the case where the average value was 1.6 or more and less than 2.6 is defined as "B"; and the case where the average value was less than 1.6 is defined as "C". The results are shown in Table 1.

<Change of Color Tone>

The first agent of each of the Examples and the Comparative Examples was preserved in a thermostat at 45° C. for one month. The hair dyeing treatment was carried out in the same manner as described above by using the first agent of each of the Examples and the Comparative Examples having been preserved for a prescribed period of time, thereby obtaining each of hair bundles. With respect to the first agent of each of the Examples and the Comparative Examples, which had not been subjected to a preservation treatment, the same hair dyeing treatment was carried out to prepare each hair bundle, which was applied as a control. With respect to each of the resulting hair bundles, the presence or absence of a change of color tone (lightness and chroma) to be caused due to the presence or absence of the preservation treatment was visually observed under a standard light source by ten expert panelists, and the evaluation was made according to the following criteria.

The results were marked with three grades in such a manner that the case where a change was not substantially observed in the hair dyeing results as compared with the control is given a score 3; the case where a change was slightly observed in the hair dyeing results as compared with the control is given a score 2; and the case where a change was observed in the hair dyeing results as compared with the control is given a score 1. With respect to the marking results by each of the expert panelists, an average value was calculated. The evaluation results are designated in such a manner that the case where the average value was 2.6 or more is defined as "A"; the case where the average value was 1.6 or more and less than 2.6 is defined as "B"; and the case where the average value was less than 1.6 is defined as "C". The results are shown in Table 1.

TABLE 1

| | <First agent> | Example 1 | Example 2 | Example 3 | Example 4 | Example 5 | Example 6 | Example 7 | Example 8 | Example 9 |
|---|---|---|---|---|---|---|---|---|---|---|
| (A) | Resorcin | 0.05 | 0.05 | 0.05 | 0.05 | 0.1 | 0.03 | 0.05 | 0.1 | 0.2 |
| (C) | p-Phenylenediamine | 0.1 | 0.1 | 0.1 | 0.1 | | 0.02 | 0.02 | 0.02 | 0.02 |
| | Toluene-2,5-diamine | | | | | 0.08 | | | | |
| | p-Aminophenol | | | | | | | | | |
| (B) | 1,5-Dihydroxynaphthalene | 0.1 | | | | 0.06 | 0.03 | 0.03 | 0.03 | 0.03 |
| | 5-(2-Hydroxyethylamino)-2-methylphenol | | 0.1 | | | | | | | |
| | 4-Nitro-o-phenylenediamine | | | 0.1 | | | 0.03 | 0.03 | 0.03 | 0.03 |
| | 2-Nitro-p-pehnylenediamine | | | | 0.1 | | | | | |
| | 2,4-Diaminophenoxyethanol hydrochloride | | | | | 0.12 | | | | |
| | POE(30) cetyl ether | 2 | 2 | 2 | 2 | 2 | 2 | 2 | 2 | 2 |
| | POE(2) cetyl ether | 1 | 1 | 1 | 1 | 1 | 1 | 1 | 1 | 1 |
| | Stearyl trimethyl ammonium chloride | 0.25 | 0.25 | 0.25 | 0.25 | 0.25 | 0.25 | 0.25 | 0.25 | 0.25 |
| | Vaseline | 3 | 3 | 3 | 3 | 3 | 3 | 3 | 3 | 3 |
| | Cetanol | 4 | 4 | 4 | 4 | 4 | 4 | 4 | 4 | 4 |
| | Stearyl alcohol | 3 | 3 | 3 | 3 | 3 | 3 | 3 | 3 | 3 |
| | L-Ascorbic acid | 0.5 | 0.5 | 0.5 | 0.5 | 0.5 | 0.5 | 0.5 | 0.5 | 0.5 |
| | 28% Ammonia water | 5.5 | 5.5 | 5.5 | 5.5 | 5.5 | 5.5 | 5.5 | 5.5 | 5.5 |
| | Ammonium hydrogencarbonate | 4 | 4 | 4 | 4 | 4 | 4 | 4 | 4 | 4 |
| | Ammonium chloride | 1.5 | 1.5 | 1.5 | 1.5 | 1.5 | 1.5 | 1.5 | 1.5 | 1.5 |
| | Purified water | Balance | Balance | Balance | Balance | Balance | Balance | Balance | Balance | Balance |
| | Whole amount | 100 | 100 | 100 | 100 | 100 | 100 | 100 | 100 | 100 |
| | Compounding amount of the component (C) in the first agent (% by mass) | 0.1 | 0.1 | 0.1 | 0.1 | 0.08 | 0.02 | 0.02 | 0.02 | 0.02 |
| | Compounding amount of the component (B) in the first agent (% by mass) | 0.1 | 0.1 | 0.1 | 0.1 | 0.06 | 0.06 | 0.06 | 0.06 | 0.06 |
| | (B)/(A) mass ratio | 2 | 2 | 2 | 2 | 0.6 | 2 | 1.2 | 0.6 | 0.3 |
| Evaluation | Lightness | A | A | A | A | A | A | A | A | A |
| | Chroma | A | A | A | A | A | A | A | A | B |
| | Change of color tone | A | A | A | A | A | A | A | A | A |

| | <First agent> | Example 10 | Example 11 | Example 12 | Example 13 | Comparative Example 1 | Comparative Example 2 | Comparative Example 3 | Comparative Example 4 | Comparative Example 5 |
|---|---|---|---|---|---|---|---|---|---|---|
| (A) | Resorcin | 0.05 | 0.05 | 0.05 | 0.03 | | | | 0.3 | 0.05 |
| (C) | p-Phenylenediamine | | | | 0.05 | 0.02 | 0.04 | | 0.02 | 0.02 |
| | Toluene-2,5-diamine | 0.32 | 0.37 | | | | | 0.08 | | |
| | p-Aminophenol | | | 0.23 | 0.2 | 0.2 | | | | |
| (B) | 1,5-Dihydroxynaphthalene | | | 0.05 | | 0.03 | | 0.06 | 0.03 | 0.03 |
| | 5-(2-Hydroxyethylamino)-2-methylphenol | 0.16 | 0.03 | 0.1 | 0.25 | | 0.06 | | | |
| | 4-Nitro-o-phenylenediamine | | 0.05 | | 0.03 | 0.03 | | | 0.03 | 0.03 |
| | 2-Nitro-p-pehnylenediamine | | | | | | | | | |
| | 2,4-Diaminophenoxyethanol hydrochloride | | | | | | | 0.12 | | |
| | POE(30) cetyl ether | 2 | 2 | 2 | 2 | 2 | 2 | 2 | 2 | 2 |
| | POE(2) cetyl ether | 1 | 1 | 1 | 1 | 1 | 1 | 1 | 1 | 1 |
| | Stearyl trimethyl ammonium chloride | 0.25 | 0.25 | 0.25 | 0.25 | 0.25 | 0.25 | 0.25 | 0.25 | 0.25 |
| | Vaseline | 3 | 3 | 3 | 3 | 3 | 3 | 3 | 3 | 3 |
| | Cetanol | 4 | 4 | 4 | 4 | 4 | 4 | 4 | 4 | 4 |
| | Stearyl alcohol | 3 | 3 | 3 | 3 | 3 | 3 | 3 | 3 | 3 |
| | L-Ascorbic acid | 0.5 | 0.5 | 0.5 | 0.5 | 0.5 | 0.5 | 0.5 | 0.5 | 0.5 |
| | 28% Ammonia water | 5.5 | 5.5 | 5.5 | 5.5 | 5.5 | 5.5 | 5.5 | 5.5 | 5.5 |
| | Ammonium hydrogencarbonate | 4 | 4 | 4 | 4 | 4 | 4 | 4 | 4 | 4 |
| | Ammonium chloride | 1.5 | 1.5 | 1.5 | 1.5 | 1.5 | 1.5 | 1.5 | 1.5 | 1.5 |
| | Purified water | Balance | Balance | Balance | Balance | Balance | Balance | Balance | Balance | Balance |
| | Whole amount | 100 | 100 | 100 | 100 | 100 | 100 | 100 | 100 | 100 |
| | Compounding amount of the component (C) in the first agent (% by mass) | 0.32 | 0.6 | 0.2 | 0.25 | 0.02 | 0.04 | 0.08 | 0.02 | 0.02 |
| | Compounding amount of the component (B) in the first agent (% by mass) | 0.16 | 0.08 | 0.15 | 0.28 | 0.06 | 0.06 | 0.06 | 0.06 | 0.06 |
| | (B)/(A) mass ratio | 3.2 | 1.6 | 3 | 9.33 | — | — | — | 0.2 | 1.2 |
| Evaluation | Lightness | A | B | A | A | A | A | A | A | C |
| | Chroma | A | A | A | A | A | A | A | C | A |
| | Change of color tone | A | A | A | A | C | C | C | B | A |

TABLE 2

| <Second agent> | |
|---|---|
| 35% Hydrogen peroxide | 15.7 |
| Hydroxyethanediphosphonic acid | 0.2 |
| Tetrasodium hydroxyethanediphosphonate | 0.3 |
| Phenoxyethanol | 0.2 |
| Microcrystalline wax | 5.0 |
| Cetanol | 4.0 |
| Stearyl alcohol | 1.0 |
| POE(30) cetyl ether | 1.0 |
| POE(2) cetyl ether | 0.5 |
| Stearyl trimethyl ammonium chloride | 4.0 |
| Vaseline | 2.0 |
| Purified water | Balance |
| Whole amount | 100 |

As shown in Table 1, it was understood that in the oxidation hair dye composition using the first agent according to each of the Examples, the evaluations in the lightness, chroma, and change of color tone are high as compared with those of the Comparative Examples.

As shown in Table 1, it was understood that Comparative Examples 1 to 3 not containing resorcin are low in the evaluation regarding the change of color tone as compared with each of the Examples. It was understood that Comparative Example 4 in which the compounding amount of resorcin in the first agent is 0.3% by mass is low in the evaluation regarding the chroma as compared with each of the Examples. It was understood that Comparative Example 5 not containing the carbonate is low in the evaluation regarding the lightness as compared with each of the Examples.

Formulation Example 2

In Formulation Example 2, the hair dye composition of the present embodiment was constituted as a first agent in a foamy form of an oxidation hair dye composition. A first agent and a second agent of an oxidation hair dye composition containing the respective components shown in Table 3, each of which was to be filled in an aerosol can and discharged in a foamy form, were prepared. Each of the first agent and the second agent shown in Table 3 was discharged in a foamy form from the aerosol can onto a brush at the time of use. It is to be noted that the first agent and the second agent were discharged in a mass ratio of 1/1. Subsequently, the same hair bundle as in Formulation Example 1 was used, and the respective agents were mixed while applying by the brush. Subsequently, a hair dyeing treatment was carried out by adopting the same method as in Formulation Example 1. Each of evaluations regarding the lightness, chroma, and change of color tone was carried out according to the method shown in Formulation Example 1. The results are shown in Table 3. It is to be noted that a comparative example which is different from Formulation Example 2 only in a point of not compounding resorcin was also carried out (data not attached).

TABLE 3

| | | Example 14 |
|---|---|---|
| | <First agent> | |
| (A) | Resorcin | 0.05 |
| (C) | p-Phenylenediamine | 0.1 |

TABLE 3-continued

| | | Example 14 |
|---|---|---|
| (B) | 1,5-Dihydroxynaphthalene | 0.1 |
| | 28% Ammonia water | 5.0 |
| | Ammonium hydrogencarbonate | 4.0 |
| | POE(10) lauryl ether | 1.5 |
| | POE(10) cetyl ether | 1.0 |
| | Alkyl (C8-C16) glucoside | 0.5 |
| | Stearyl trimethyl ammonium chloride | 0.5 |
| | Glycerin | 2.0 |
| | Cetanol | 0.7 |
| | Behenyl alcohol | 0.3 |
| | Olive oil | 3.0 |
| | Merquat 100 | 0.5 |
| | Sodium sulfite | 0.3 |
| | Sodium diethylenetriaminepentaacetate | 0.3 |
| | Ascorbic acid | 0.5 |
| | Purified water | Balance |
| | Whole amount | 100.0 |
| | Undiluted solution of the above-described components/propellant (LPG) ratio | 95:5 |
| | <Second agent> | |
| | Myristyl alcohol | 0.2 |
| | Cetanol | 1.0 |
| | POE(10) lauryl ether | 0.5 |
| | POE(30) cetyl ether | 0.5 |
| | Stearyl trimethyl ammonium chloride | 0.2 |
| | Hydroxyethanediphosphonic acid | 0.1 |
| | Tetrasodium hydroxyethanediphosphonate | 0.2 |
| | Phenoxyethanol | 0.1 |
| | Phosphoric acid | Amount to be regulated to pH 3 |
| | 35% hydrogen peroxide | 15.0 |
| | Purified water | Balance |
| | Whole amount | 100.0 |
| | Undiluted solution of the above-described components/propellant (LPG) ratio | 95:5 |
| Evaluation | Lightness | A |
| | Chroma | A |
| | Change of color tone | A |

As shown in Table 3, it was understood that in the present formulation, in particular, the evaluation regarding the change of color tone and the like is high, too as compared with the Comparative Example.

Formulation Example 3

In Formulation Example 3, the hair dye composition of the present embodiment was constituted as a first agent in a cream form of an oxidation hair dye composition. A first agent and a second agent of an oxidation hair dye composition containing the respective components shown in Table 4, each of which was to be filled in an aerosol can and discharged in a cream form, were prepared. Each of the first agent and the second agent shown in Table 4 was discharged in a cream form from the aerosol can onto a brush at the time of use. It is to be noted that the first agent and the second agent were discharged in a mass ratio of 1/1. Subsequently, the same hair bundle as in Formulation Example 1 was used, and the respective agents were mixed while applying by the brush. Subsequently, a hair dyeing treatment was carried out by adopting the same method as in Formulation Example 1. Each of evaluations regarding the lightness, chroma, and change of color tone was carried out according to the method shown in Formulation Example 1. The results are shown in Table 4. It is to be noted that a comparative example which is different from Formulation Example 3 only in a point of not compounding resorcin was also carried out (data not attached).

TABLE 4

|  |  | Example 15 |
|---|---|---|
|  | <First agent> |  |
| (A) | Resorcin | 0.05 |
| (C) | p-Phenylenediamine | 0.1 |
| (B) | 1,5-Dihydroxynaphthalene | 0.1 |
|  | 28% Ammonia water | 5.0 |
|  | Ammonium hydrogencarbonate | 4.0 |
|  | POE(30) cetyl ether | 2.0 |
|  | POE(2) cetyl ether | 1.0 |
|  | Stearyl trimethyl ammonium chloride | 0.25 |
|  | Vaseline | 3.0 |
|  | Cetanol | 4.0 |
|  | Stearyl alcohol | 3.0 |
|  | Ascorbic acid | 0.5 |
|  | Purified water | Balance |
|  | Whole amount | 100.0 |
|  | Undiluted solution of the above-described components/propellant (nitrogen gas) ratio | 95:5 |
|  | <Second agent> |  |
|  | Stearyl alcohol | 1.0 |
|  | Cetanol | 4.0 |
|  | POE(30) cetyl ether | 1.0 |
|  | POE(2) cetyl ether | 0.5 |
|  | Stearyl trimethyl ammonium chloride | 2.0 |
|  | Vaseline | 2.0 |
|  | Microcrystalline wax | 5.0 |
|  | Phenoxyethanol | 0.2 |
|  | Hydroxyethanediphosphonic acid | 0.2 |
|  | Tetrasodium hydroxyethanediphosphonate | 0.3 |
|  | Phosphoric acid | Amount to be regulated to pH 3 |
|  | 35% hydrogen peroxide | 15.0 |
|  | Purified water | Balance |
|  | Whole amount | 100.0 |
|  | Undiluted solution of the above-described components/propellant (nitrogen gas) ratio | 95:5 |
| Evaluation | Lightness | A |
|  | Chroma | A |
|  | Change of color tone | A |

As shown in Table 4, it was understood that in the present formulation, in particular, the evaluation regarding the change of color tone and the like is high, too as compared with the Comparative Example.

Formulation Example 4

In Formulation Example 4, the hair dye composition of the present embodiment was constituted as a first agent in a gel emulsion form of an oxidation hair dye composition. A first agent in a gel emulsion form and a second agent in a liquid form of an oxidation hair dye composition containing the respective components shown in Table 5 were prepared. Then, the first agent and the second agent were mixed in a mass ratio of 1/1 to prepare an oxidation hair dye composition. Subsequently, a hair dyeing treatment was carried out by adopting the same method as in Formulation Example 1. Each of evaluations regarding the lightness, chroma, and change of color tone was carried out according to the method shown in Formulation Example 1. The results are shown in Table 5. It is to be noted that a comparative example which is different from Formulation Example 4 only in a point of not compounding resorcin was also carried out (data not attached).

TABLE 5

|  |  | Example 16 |
|---|---|---|
|  | <First agent> |  |
| (A) | Resorcin | 0.05 |
| (C) | p-Phenylenediamine | 0.1 |
| (B) | 1,5-Dihydroxynaphthalene | 0.1 |
|  | 28% Ammonia water | 5.0 |
|  | Ammonium hydrogencarbonate | 4.0 |
|  | POE(3) oleyl ether phosphate | 5.0 |
|  | POE(3) alkyl (C12-C14) ether | 10.0 |
|  | Myristyl alcohol | 2.0 |
|  | Isostearyl alcohol | 3.0 |
|  | Glycerin | 3.0 |
|  | Ammonium chloride | 0.1 |
|  | Anhydrous sodium sulfite | 0.5 |
|  | Sodium ethylenediaminehydroxyethyltriacetate | 0.5 |
|  | Ascorbic acid | 0.5 |
|  | Purified water | Balance |
|  | Whole amount | 100.0 |
|  | <Second agent> |  |
|  | Stearyl alcohol | 2.0 |
|  | POE(20) stearyl ether | 1.0 |
|  | Stearyl trimethyl ammonium chloride | 0.5 |
|  | Propylene glycol | 3.0 |
|  | Diglycerin | 3.0 |
|  | Phosphoric acid | Amount to be regulated to pH 3 |
|  | 35% hydrogen peroxide | 15.0 |
|  | Purified water | Balance |
|  | Whole amount | 100.0 |
| Evaluation | Lightness | A |
|  | Chroma | A |
|  | Change of color tone | A |

As shown in Table 5, it was understood that in the present formulation, in particular, the evaluation regarding the change of color tone and the like is high, too as compared with the Comparative Example.

Formulation Example 5

In Formulation Example 5, the hair dye composition of the present embodiment was constituted as a first agent in a gel form of an oxidation hair dye composition. A first agent in a gel form and a second agent in a liquid form of an oxidation hair dye composition containing the respective components shown in Table 6 were prepared. Then, the first agent and the second agent were mixed in a mass ratio of 1/1 to prepare an oxidation hair dye composition. Subsequently, a hair dyeing treatment was carried out by adopting the same method as in Formulation Example 1. Each of evaluations regarding the lightness, chroma, and change of color tone was carried out according to the method shown in Formulation Example 1. The results are shown in Table 6. It is to be noted that a comparative example which is different from Formulation Example 5 only in a point of not compounding resorcin was also carried out (data not attached).

TABLE 6

|  |  | Example 17 |
|---|---|---|
|  | <First agent> |  |
| (A) | Resorcin | 0.05 |
| (C) | p-Phenylenediamine | 0.1 |

TABLE 6-continued

| | | Example 17 |
|---|---|---|
| (B) | 1,5-Dihydroxynaphthalene | 0.1 |
| | 28% Ammonia water | 5.0 |
| | Ammonium hydrogencarbonate | 4.0 |
| | Myristyl alcohol | 2.0 |
| | Isostearyl alcohol | 3.0 |
| | Xanthan gum | 3.0 |
| | Glycerin | 3.0 |
| | Ammonium chloride | 0.1 |
| | Anhydrous sodium sulfite | 0.5 |
| | Sodium ethylenediaminehydroxyethyltriacetate | 0.5 |
| | Ascorbic acid | 0.5 |
| | Purified water | Balance |
| | Whole amount | 100.0 |
| | <Second agent> | |
| | Stearyl alcohol | 2.0 |
| | POE(20) stearyl ether | 1.0 |
| | Stearyl trimethyl ammonium chloride | 0.5 |
| | Propylene glycol | 3.0 |
| | Diglycerin | 3.0 |
| | Phosphoric acid | Amount to be regulated to pH 3 |
| | 35% hydrogen peroxide | 15.0 |
| | Purified water | Balance |
| | Whole amount | 100.0 |
| Evaluation | Lightness | A |
| | Chroma | A |
| | Change of color tone | A |

As shown in Table 6, it was understood that in the present formulation, in particular, the evaluation regarding the change of color tone and the like is high, too as compared with the Comparative Example.

Formulation Example 6

In Formulation Example 6, the hair dye composition of the present embodiment was constituted as a first agent in a liquid form of an oxidation hair dye composition. A first agent in a liquid form and a second agent in a liquid form of an oxidation hair dye composition containing the respective components shown in Table 7 were prepared. Then, the first agent and the second agent were mixed in a mass ratio of 1/1 to prepare an oxidation hair dye composition. Subsequently, a hair dyeing treatment was carried out by adopting the same method as in Formulation Example 1. Each of evaluations regarding the lightness, chroma, and change of color tone was carried out according to the method shown in Formulation Example 1. The results are shown in Table 7. It is to be noted that a comparative example which is different from Formulation Example 6 only in a point of not compounding resorcin was also carried out (data not attached).

TABLE 7

| | | Example 18 |
|---|---|---|
| | <First agent> | |
| (A) | Resorcin | 0.05 |
| (C) | p-Phenylenediamine | 0.1 |
| (B) | 1,5-Dihydroxynaphthalene | 0.1 |
| | 28% Ammonia water | 5.0 |
| | Ammonium hydrogencarbonate | 4.0 |
| | POE(6) oleyl ether | 20.0 |
| | Lauryl dimethylaminoacetic acid betaine | 5.0 |
| | Sodium lauryl sulfate | 5.0 |

TABLE 7-continued

| | | Example 18 |
|---|---|---|
| | Lanolin fatty acid amidopropyl ethyldimethyl ammonium ethyl sulfate | 0.5 |
| | Oleic acid | 10.0 |
| | Ethanol | 8.0 |
| | Polyethylene glycol 1000 | 20.0 |
| | Sodium sulfite | 0.5 |
| | Edetate disodium | 0.5 |
| | Ascorbic acid | 0.5 |
| | Purified water | Balance |
| | Whole amount | 100.0 |
| | <Second agent> | |
| | Cetanol | 2.0 |
| | Sodium lauryl sulfate | 0.5 |
| | Phosphoric acid | Amount to be regulated to pH 3 |
| | Edetate disodium | 0.5 |
| | 35% hydrogen peroxide | 15.0 |
| | Purified water | Balance |
| | Whole amount | 100.0 |
| Evaluation | Lightness | A |
| | Chroma | A |
| | Change of color tone | A |

As shown in Table 7, it was understood that in the present formulation, in particular, the evaluation regarding the change of color tone and the like is high, too as compared with the Comparative Example.

Reference Formulation Example 1

0.05% by mass of resorcin, 0.5% by mass of isononyl isononanoate, 2.5% by mass of stearic acid dimethylaminopropylamide, 0.5% by mass of HC Blue No. 2, 0.1% by mass of HC Yellow No. 4, 0.1% by mass of 4-nitro-o-phenylenediamine, 8% by mass of cetostearyl alcohol, 0.5% by mass of bee wax, 3% by mass of liquid paraffin, 2% by mass of glycerin, 0.5% by mass of lactic acid, 0.3% by mass of phenoxyethanol, 0.5% by mass of dimethylpolysiloxane, 0.5% by mass of a perfume, and a balance of purified water were mixed to prepare a semi-permanent hair dye (color treatment) of Reference Formulation Example 1. In addition, a color treatment of Reference Comparative Example 1 which is different from the constitution of Reference Formulation Example 1 only in a point of not compounding resorcin was prepared.

Each of the obtained color treatments was applied to a bundle of human white hair (15 cm, available from Beaulax Co., Ltd.) by using a brush and then allowed to stand at room temperature (25° C.) for 30 minutes. Subsequently, the semi-permanent hair dye attached onto the hair bundle was washed off with water. Subsequently, the hair bundle was dried with warm air and then allowed to stand for one day. Each of the hair bundles having been subjected to the hair dyeing treatment was evaluated with respect to a change of the color tone according to the same method as in Formulation Example 1.

As a result, it was confirmed that in Reference Formulation Example 1, the evaluation regarding the change of color tone was high (that is, the change was small) as compared with Reference Comparative Example 1. In the above-described embodiment, even in the case of further constituting a semi-permanent hair dye containing 0.2% by mass or less of resorcin and a nitro dye as the component (B)

without using the carbonate, it was confirmed that the effect for improving the stability of the dye due to resorcin is obtained.

Reference Formulation Example 2

0.05% by mass of resorcin, 0.1% by mass of 4-nitro-o-phenylenediamine, 0.2% by mass of Black Color No. 401, 0.05% by mass of Red Color No. 106, 0.5% by mass of HC Blue No. 2, 0.1% by mass of HC Yellow No. 4, 3% by mass of hydroxyethyl cellulose, 2.5% by mass of lactic acid (50%), 4.5% by mass of diethoxyethyl succinate, 0.5% by mass of benzyl alcohol, 5% by mass of ethanol, 0.3% by mass of a perfume, and a balance of pure water were mixed to prepare a semi-permanent hair dye (hair manicure) of Reference Formulation Example 2. In addition, a hair manicure of Reference Comparative Example 2 which is different from the constitution of Reference Formulation Example 2 only in a point of not compounding resorcin was prepared. Subsequently, the hair dyeing treatment was carried out by adopting the same method as in Formulation Example 1. Each of the hair bundles having been subjected to the hair dyeing treatment was evaluated with respect to a change of the color tone according to the same method as in Formulation Example 1.

As a result, it was confirmed that in Reference Formulation Example 2, the evaluation regarding the change of color tone was high as compared with Reference Comparative Example 2.

Next, technical ideas that can be grasped from the above-described embodiments and the modifications are described additionally below along with effects thereof.

(a) The above-described hair dye composition, which is used for fashion color. The hair dye composition of the present invention has excellent lightness and chroma, and hence, it can be suitably used especially in the field of fashion color.

(b) A semi-permanent hair dye comprising (A) at least one selected from resorcin and its derivative, and salts thereof, an upper limit of a compounding amount of the component (A) being 0.2% by mass or less, and (b) a nitro dye.

(c) A method for stabilizing a color tone of dyed hair by a semi-permanent hair dye, the method comprising compounding (A) at least one selected from resorcin and its derivatives, and salts thereof, an upper limit of a compounding amount of the component (A) being 0.2% by mass or less, and (b) a nitro dye. In the constitutions (b) and (c), the stability of the nitro dye (b) can be improved by the component (A).

(d) The above-described semi-permanent hair dye, wherein the nitro dye (b) is at least one selected from 4-nitro-o-phenylenediamine, 2-nitro-p-phenylenediamine, 2-amino-4-nitrophenol, HC Blue No. 2, and HC Yellow No. 4. The color tone can be more stabilized, and excellent lightness and chroma can be given to a hair.

The invention claimed is:

1. A hair dye composition containing a carbonate, which further comprises
   (I) a first agent comprising
   (A) 0.03 to 0.1% by mass of at least one selected from resorcin and its derivatives, and salts thereof,
   (B) 0.06 to 0.28% by mass of at least one dye selected from 5-(2-hydroxyethylamino)-2-methylphenol, 1,5-dihydroxy naphthalene and a nitro dye, and
   (C) 0.02 to 0.32% by mass of a dye intermediate selected from p-phenylenediamine, toluene-2,5-diamine and p-aminophenol,
   wherein a ratio B/A is in a range of 0.6 to 9.33; and
   (II) a second agent containing an oxidizing agent.

2. A method of dyeing hair with a hair dye composition containing a carbonate in a first agent, the method comprising compounding, as the first agent of the hair dye composition, together with the carbonate,
   (A) 0.03 to 0.1% by mass of at least one selected from resorcin and its derivatives, and salts-thereof,
   (B) 0.03 to 0.28% by mass of at least one dye selected from 5-(2-hydroxyethylamino)-2-methylphenol, 1,5-dihydroxynaphthalene and a nitro dye, and
   (C) 0.02 to 0.32% by mass of a dye intermediate selected from p-phenylenediamine, toluene-2,5-diamine and p-aminophenol,
   wherein a ratio B/A is in a range of 0.6 to 9.33; and
   providing, as a second agent, a composition comprising an oxidizing agent;
   mixing the first and second agents together; and
   subsequently applying the mixture to hair.

3. A method of dyeing hair, comprising applying to hair the hair dye composition of claim 1.

4. A hair dye composition containing a carbonate according to claim 1, which further comprises ammonia and/or salts thereof.

5. A method of dyeing hair, comprising applying to hair the hair dye composition of claim 4.

6. The hair dye composition containing a carbonate according to claim 1, wherein the nitro dye is at least one selected from 4-nitro-o-phenylenediamine and 2-nitro-p-phenylenediamine.

7. A method of dyeing hair, comprising applying to hair the hair dye composition of claim 6.

* * * * *